(12) United States Patent
Van Heijkamp et al.

(10) Patent No.: US 10,517,356 B2
(45) Date of Patent: Dec. 31, 2019

(54) METHOD AND MACHINE FOR PREPARING INSOLES

(71) Applicant: TO-A-T IP B.V., Munich (DE)

(72) Inventors: Caroline Margarethe Van Heijkamp, De Bilt (NL); Léon Ferdinand Van Heijkamp, The Hague (NL); Georgius Josephus Maria Hersbach, Loosdrecht (NL)

(73) Assignee: TO-A-T IP B.V., Munich (DE)

( * ) Notice: Subject to any disclaimer, the term of this patent is extended or adjusted under 35 U.S.C. 154(b) by 29 days.

(21) Appl. No.: 15/578,270

(22) PCT Filed: Jun. 3, 2016

(86) PCT No.: PCT/EP2016/062711
§ 371 (c)(1),
(2) Date: Nov. 30, 2017

(87) PCT Pub. No.: WO2016/193469
PCT Pub. Date: Dec. 8, 2016

(65) Prior Publication Data
US 2018/0140053 A1     May 24, 2018

(30) Foreign Application Priority Data

Jun. 3, 2015 (EP) .................................. 15170578

(51) Int. Cl.
*A43D 1/00* (2006.01)
*G05B 19/4099* (2006.01)
(Continued)

(52) U.S. Cl.
CPC .............. *A43D 1/025* (2013.01); *A43B 17/00* (2013.01); *B29C 64/386* (2017.08); *B33Y 50/00* (2014.12);
(Continued)

(58) Field of Classification Search
CPC .... A43D 1/025; A43D 2200/60; B33Y 50/00; B33Y 80/00; G05B 19/4099;
(Continued)

(56) References Cited

U.S. PATENT DOCUMENTS 4,866,802 A * 9/1989 Stein ...................... A43D 37/00
12/1 A
5,339,252 A * 8/1994 White .................... A43D 1/025
12/146 L
(Continued)

FOREIGN PATENT DOCUMENTS

CN     104282039     1/2015
DE     102007032609     3/2009
(Continued)

OTHER PUBLICATIONS

NPL Pedar®-x system, pp. 2, circa 2008 (Year: 2008).*
(Continued)

*Primary Examiner* — Ronald D Hartman, Jr.
(74) *Attorney, Agent, or Firm* — Mark M. Friedman (57) ABSTRACT

The present invention relates to a method of preparing insoles and to a system for preparing insoles. The invention uses a machine for imaging the foot inserted in the footwear, designs an insole and produces the insole for instance with a three dimensional printer.

17 Claims, 5 Drawing Sheets

(51) Int. Cl.
*A43D 1/02* (2006.01)
*B33Y 80/00* (2015.01)
*B33Y 50/00* (2015.01)
*B29C 64/386* (2017.01)
*A43B 17/00* (2006.01)

(52) U.S. Cl.
CPC .......... *B33Y 80/00* (2014.12); *G05B 19/4099* (2013.01); *A43D 2200/60* (2013.01); *G05B 2219/35134* (2013.01); *G05B 2219/49007* (2013.01)

(58) Field of Classification Search
CPC .......... G05B 2219/35134; G05B 2219/49007; A43B 17/00; A43B 17/14; B29C 64/386; A61B 6/00; A61B 6/505; A61B 6/032
See application file for complete search history.

(56) References Cited

U.S. PATENT DOCUMENTS

| | | | | |
|---|---|---|---|---|
| 5,807,449 | A * | 9/1998 | Hooker | A43D 25/183 118/680 |
| 6,438,780 | B1 * | 8/2002 | Hansen | B62D 1/28 12/1 A |
| 6,741,728 | B1 * | 5/2004 | Genest | A43D 1/02 382/115 |
| 6,975,232 | B1 * | 12/2005 | McKenna | A43D 1/025 340/573.1 |
| 7,657,100 | B2 * | 2/2010 | Gokturk | G06K 9/46 382/209 |
| 8,325,874 | B2 | 12/2012 | Shi et al. | |
| 8,548,120 | B2 | 4/2013 | Shi et al. | |
| 10,013,711 | B2 * | 7/2018 | Gooch | G06Q 30/0631 |
| 2004/0168329 | A1 * | 9/2004 | Ishimaru | A43D 1/02 33/3 R |
| 2005/0049816 | A1 * | 3/2005 | Oda | A43D 1/025 702/127 |
| 2005/0061332 | A1 * | 3/2005 | Greenawalt | A43D 1/025 128/882 |
| 2006/0070260 | A1 * | 4/2006 | Cavanagh | A43B 17/00 36/44 |
| 2006/0143839 | A1 * | 7/2006 | Fromme | A43B 7/00 12/142 R |
| 2009/0051683 | A1 * | 2/2009 | Goonetilleke | A43D 1/025 345/419 |
| 2009/0247909 | A1 * | 10/2009 | Mukumoto | A43B 7/28 600/592 |
| 2011/0055053 | A1 * | 3/2011 | Rutschmann | G06Q 10/087 705/27.2 |
| 2011/0123099 | A1 * | 5/2011 | Pfeiffer | A43D 1/06 382/154 |
| 2011/0232008 | A1 * | 9/2011 | Crisp | A43B 9/00 12/18.1 |
| 2013/0094748 | A1 | 4/2013 | Shi et al. | |
| 2013/0296740 | A1 * | 11/2013 | Greenawalt | A61B 5/1036 600/592 |
| 2014/0149072 | A1 * | 5/2014 | Rutschmann | A43D 1/022 702/167 |
| 2014/0277658 | A1 * | 9/2014 | Hanft | G05B 15/02 700/97 |
| 2014/0285646 | A1 * | 9/2014 | Kahlon | A43D 1/025 348/77 |
| 2015/0165690 | A1 * | 6/2015 | Tow | B33Y 80/00 700/119 |
| 2016/0081435 | A1 * | 3/2016 | Marks | A43D 1/027 382/154 |
| 2016/0125499 | A1 * | 5/2016 | Gooch | G06Q 30/0631 705/26.7 |
| 2016/0345666 | A1 * | 12/2016 | Kohatsu | A43B 13/186 |
| 2017/0053335 | A1 * | 2/2017 | Hanscom | A43D 1/025 |

FOREIGN PATENT DOCUMENTS

| | | |
|---|---|---|
| KR | 2814 8147443 | 12/2014 |
| WO | 2004073441 | 9/2004 |
| WO | 2005111539 | 1/2005 |
| WO | 2007044417 | 4/2007 |
| WO | 2011014786 | 2/2011 |
| WO | 2014014977 | 1/2014 |

OTHER PUBLICATIONS

John B. Ludlow et al; Weightbearing CBCT, MDCT, and 2D imaging dosimetry of the foot and ankle, in International Journal of Diagnostic Imaging, 2014, vol. 1, No. 2.
"Crossover Innovation Challenge", Apr. 11, 2015 in http://www.kennispoortregiozwolle.nl/workshops-details-xic/-/items/op-goede-voet-met-innovatie.html.
Pedar x;http://www.syna-med.com.tw/pdf/pedarX_eng.pdf.
Pedcat brochure.
Screenshot Apr. 10, 2015.WWw.Curvebeam/videos.

* cited by examiner

METHOD AND MACHINE FOR PREPARING INSOLES

TECHNICAL FIELD

The present invention relates to a method of designing an insole for a foot inserted in footwear and preparing an insole, to a computer implemented method, and to a system.

BACKGROUND TO THE INVENTION

Insoles for footwear are generally made of plastic (chemical polymers) and/or leather. They are often made in factories in standard size and large numbers and do, by nature, not accommodate different feet correctly or optimally. Orthopedic insoles are generally custom-made to accommodate the specific foot print of the human subject. However, production involves extensive measuring and manual labor. Consequently, we have identified a challenge in the art to produce custom-made insoles that do not require extensive measuring, manual custom-made labor, during an extensive time and/or for high costs.

SUMMARY OF THE INVENTION

Accordingly, the invention provides a method for preparing custom-made insoles that offer an optimal fit of a particular foot in a particular footwear, allowing for different feet and for footwear of different size and shape, in an automated manner with limited waste, in a short time and/or with limited effort.

Accordingly, the invention relates to a method of preparing an insole for a foot inserted in footwear by:
  inserting the foot in the footwear;
  positioning the foot, inserted in the footwear, in an imaging machine;
  scanning the foot inserted in the footwear with the imaging machine;
  determining a space between the foot and an inner surface of the footwear; and
  designing an insole that fills at least part of the space between the foot and the footwear inner surface.

Preferably, the insole design is provided to a printer machine to produce the insole. Preferably, the footwear is in a fixated position in the imaging machine during the scanning. Preferably, the imaging machine produces a digital, three dimensional image of the foot and footwear. Preferably, first a flexible container is inserted in the footwear and subsequently the foot is inserted in the footwear. Preferably, the flexible container has one or more compartments that are inflated with a medium before, during or after the scanning with the imaging machine. Preferably, determining the space between the foot and an inner surface of the footwear comprises of determining the position of one or more bones and/or skin of the foot and the inner surface of the footwear. Preferably, determining the space between the foot and an inner surface of the footwear comprises of determining the position of one or more bones and/or soft tissue and/or skin of the foot and the inner surface of the footwear. Preferably, determination of the space is conducted three dimensionally and digitally. Preferably, the image of the foot inserted in the footwear is presented on a display. Preferably, determining a space between the foot and the inner surface of the footwear comprises using image data from the imaging machine and generating three dimensional profiles of the footwear and of the foot. Preferably, designing the insole that fills at least part of the space between the foot and the footwear inner surface comprises generating a digital three dimensional image of the insole that has a lower profile that follows the footwear inner surface, that has an upper profile that follows the bottom of the foot, and that has an inner insole structure that connects both profiles.

In another aspect, the invention relates to a computer implemented method for designing an insole comprising the following steps:
  directing an X-ray machine to scan a foot inserted in footwear;
  producing an image resulting from the scan using the X-ray machine's image detection system;
  determining a space between the foot and an inner surface of the footwear on the image;
  using algorithms designing an insole that fills at least part of the space between the foot and the footwear inner surface.

Preferably, the computer implemented method further comprises the step of instructing a three dimensional printer to produce the insole.

In another aspect, the invention relates to a system comprising an imaging machine, a computer and a printer machine which are connected in an electronic network, wherein the imaging machine is a X-ray machine for producing three dimensional X-ray images and the printer is a three dimensional printer for producing three dimensional insoles.

In a further aspect, the invention relates to a system comprising an imaging machine, a computer and a printer machine which are connected in an electronic network, wherein the imaging machine is adapted for producing images of a foot and a footwear, the computer is adapted for determining a space between the foot and the footwear from the images, and the printer is a three dimensional printer adapted for producing an insole for the space between the foot and the footwear. Preferably, the imaging machine comprises at least one piece of footwear.

The present invention allows in particular for preparing insoles that are optimized for the interaction between in principle any specific foot and any specific footwear, even under real-life, weight-bearing conditions. This is achieved by imaging the foot inside the footwear, allowing for imaging of their intimate interaction, preferably three dimensionally. The image of the real-life interaction can then be used to design the insole to provide optimal support and/or correction. The optimal insole can then be prepared, preferably in a printer machine. All these steps can be carried digitally, increasing the speed, reducing effort and waiting time, but also increasing the accuracy in order to achieve the optimal fit of foot and footwear under real-life, even weight bearing conditions with the insole designed according to the steps of the invention.

Preferably, the present invention further relates to a method of designing an insole for a foot inserted in footwear by:
  inserting the foot in the footwear;
  positioning the foot, inserted in the footwear, in an imaging machine;
  generating an image of the foot inserted in the footwear with the imaging machine;
  determining from the image a space between the foot and an inner surface of the footwear;
  designing an insole that fills at least part of the space between the foot and the footwear inner surface.

Preferably, the insole is subsequently prepared.

In a preferred embodiment, the invention relates to a method of designing an insole for a foot for footwear by:

generating an image of a foot inserted in the footwear;
using the image to identify a space between the foot and the footwear; and
designing an insole that fills at least part of the space.

Preferably, the imaging machine generates an image. Preferably, the image is used to identify a space between the foot and the footwear. Preferably, the step of using the image to identify a space between the foot and the footwear uses contrast differences in the image to identify one or more positions selected from of one or more elements of the foot (preferably foot skin, foot soft tissue and/or foot bone), one or more elements of the footwear and/or one or more air pockets. Preferably, the positions more of these positions are identified relatively to each other in space (i.e. in 3D).

Preferably, the invention further relates to designing an insole that fills at least part of the space between the foot and the footwear inner surface. Preferably, the one or more identified positions selected from one or more elements of the foot, one or more elements of the footwear and/or one or more air pockets are used to generate a three dimensional lower profile of the top of the inner sole of the footwear and a three dimensional upper profile of the bottom of the foot.

Preferably, the lower profile and the upper profile are used to generate a three dimensional image of an insole.

BRIEF DESCRIPTION OF THE FIGURES

FIG. 7 shows a graphical representation of the insole with the lower and upper profiles and a rim, wherein the inner structure is filled-in.

DETAILED DESCRIPTION OF THE INVENTION

For the purpose of the invention, an insole is defined as the material placed on the inside of footwear, under the foot. The insole of the invention may be referred to as an arch support, support soles, a podological support soles, an inlay, an orthose, an orthopedic orthose, orthotic, and/or support inlays. Preferably, the insole is reversibly removable from the footwear. However, the invention can in principle also be used to prepare a solid sole, for instance for a slipper or a flat surface or a sole or insole that is subsequently used to make footwear of.

For the purpose of the invention, the insole is defined as having a lower profile, an inner insole structure, an upper profile and a rim. One side of the insole is the heal part for positioning at the back of the footwear, the other side the front part. The lower profile, the upper profiles and the rim represent the insole's surfaces. The insole can be made for the right foot or for the left foot.

For the purpose of the invention, the "object" is defined as the foot inserted in footwear. It will be understood from the description that, optionally, other features (such as the flexible container) may be present. The footwear can be for the right foot or for the left foot. Preferably, the right and left feet of the same subject are scanned at the same time.

For the purpose of the invention, a printer machine is defined as a machine that makes three dimensional items using a digital (electronic) file as input. In the case of the invention, the item is one or more insoles.

For the purpose of the invention, the resolution of a 3D (3-Dimensional) image is defined in terms of voxel size, a term well-known in the art for instance representing the 3D equivalent of the 2D pixel.

For the purpose of the invention, the scanning volume of the imaging machine is defined as the 3D space that is available for one or more objects to be subjected to scanning.

The present invention relates to a method for preparing an insole for a foot in footwear. The invention allows for preparation of an insole for a foot in footwear.

The invention relates to an imaging process using the following steps:
inserting the foot in the footwear;
positioning the foot, inserted in the footwear, in the imaging machine; and
scanning the foot inserted in the footwear with an imaging machine.

The invention also provides for scanning of both foot-in-footwear at the same time, allowing for quicker scanning which might more accurately reflect the weight bearing of each foot-in-footwear. It will be understood that, in the application as appropriate, reference to foot, footwear and/or foot in footwear equally applies to both feet, both footwear and/or both feet in their respective footwear. The right foot in footwear can be scanned and/or the left foot in footwear can be scanned. Preferably, both are scanned at the same time. Preferably, both feet—the left and the right—are of one subject.

The method of the invention allows for preparation of insoles for various types of feet, including healthy feet and diseased feet in regular position or in compromised position.

Preferably, the footwear has a space for the foot to rest upon, preferably an inner sole. The footwear may fully encloses the foot, such as for instance in case of in a (regular or dress) shoe, an orthopedic shoe, or boot; each with or without a heel to relatively lift the rear or hind of the foot. The footwear may also partially enclose the foot, such as in a sandal or slipper, or not enclose the foot at all, such as on a flat surface that can thus be adjusted to accommodate the shape of a foot.

Preferably, the foot and footwear is positioned in the imaging machine in a fixated position. This allows for reference of the foot and footwear elements to a fixed location and assists in the imaging process as well as in creating a proper real-life image. But, of course, also one or more elements of the foot or footwear can function as such a reference for building the image. In any event, fixating the footwear during scanning improves the image quality. Preferably, scanning is conducted three dimensionally. Preferably, the scanning produces a three dimensional image of the foot and the footwear wherein the foot is positioned inside the footwear. Preferably, at least one foot is weight bearing during the imaging process. This may help in creating an optimal image of the foot and footwear interaction to be able to design an insole with optimal support and/or correction.

The imaging machine of the invention is preferably a three dimensional imaging machine. It may be an ultrasonic sound machine but is preferably an X-ray machine. The imaging machine preferably uses ultrasonic sound and/or electromagnetic radiation. More preferably, the imaging machine uses X-ray. According to the invention, the imaging machine comprises a generator and an image detection system and the preferred X-ray machine comprises an X-ray source (which is sometimes called an X-ray tube) as generator. Preferably, the imaging machine comprises a digital image detection system allowing for direct digital image processing according to the invention.

To produce two and preferably three dimensional images, the X-ray machine preferably produces an X-ray computed tomography scan, sometimes called CAT or CT scan. Such CAT scans use X-ray to produce multiple cross-sectional images that are each taken from a different angle. These images together form a three dimensional image of the object (foot-in-footwear). Preferably, the imaging machine uses X-ray, electromagnetic radiation, preferably with a wavelength of 0.01 to 10 nm.

Preferably, the imaging machine uses a relatively low dose. A preferred imaging machine according to the present invention is the pedCAT® ("pedCAT"), CurveBeam, Warrington, Pa., USA. The radiation exposure of the pedCAT is comparable with that of only 10 conventional X-ray photos using modern digital technology and about 5% of conventional computer tomography of foot and ankle joint. A pedCAT scan of both feet of an adult subject gives a radiation exposure of 6.4 micro Sieverts which is less than the daily background radiation exposure in The Netherlands. Another option is the EOS imaging technology of the company EOS imaging SA, Mercoeur, Paris, France.

Preferably, Computer Aided Tomography (CAT) is used where radial X-ray scans at different heights are processed by a computer and converted via a radon transform to a set of intensity slices. These 2D images are combined by stacking into a volume data set and this data set can be used for 3D-imaging.

According to the invention, the scanning volume preferably has a length times width of from 0.2 to 0.8 $m^2$, more preferably around 0.5 $m^2$ and has a height of preferably from 0.3 to 0.5 m, more preferably 0.4 m. Preferably the scanning volume covering a volume of from 0.1 to 0.3 $m^3$, more preferably about 0.2 $m^3$ (200 liters). Preferably, the scanning volume allows for scanning of at least one foot-in-footwear, more preferably two sets of foot-in-footwear at the same time.

As an example, the pedCAT® scans multiple horizontal planes of 950×950 pixels in the x and y direction with 533 equidistant heights in the z-direction, spaced equally such that the resolution is equal in all three dimensions. The volume date set consists of a total amount of 950×950×533=481 million voxels which, multiplied by the volume per voxel gives a total scan volume of 178 liters which allows for scanning of two sets of foot-in-footwear.

Preferably, the computer uses the image obtained from the scanning step in the imaging machine as input for constructing a three dimensional image of the foot inserted in the footwear. Preferably, this image is digital. The image of the at least one foot-in-footwear preferably uses voxels with volume of at least 0.1 $mm^3$, more preferably at least 0.2 $mm^3$, most preferably at least 0.3 $mm^3$ and preferably at most 1.0, $mm^3$, more preferably at most 0.7 $mm^3$, most preferably at most 0.4 $mm^3$. As an example, the smallest resolution of the commercially available pedCAT® is approximately 0.37 $mm^3$ per voxel with dx, dy and dz each about 0.72 mm. This means that the features can be resolved below 1 mm, allowing for optimal insole production according to the invention.

Preferably, the three dimensional image of the foot inserted in the footwear is created with a computer. This computer may be integrated in the imaging machine or be a separate unit, but is preferably connected to the imaging machine to facilitate easy and fast information exchange contributing to the invention. The computer is preferably connected to a display for digitally presenting the image of the foot, of the footwear and/or of both on the display screen.

According to a preferred embodiment, the invention relates to a method that uses a flexible container. Preferably, the flexible container comprises at least two sides encompassing an internal space. Preferably the sides are made from flexible material, preferably a plastic. Examples of suitable plastics are polyvinylchloride (PVC) or poly ethylene vinyl acetate (EVA), etc.

The internal space comprises at least one compartment wherein each of the at least one compartment preferably has at least one inlet. Preferably, the internal space has at least 2, and more preferably more than 2 compartments, and preferably up to 50, for instance up to 20 compartments. Preferably, each of the at least one compartment has an inlet. Preferably a medium can introduced through the inlet into the at least one compartment to inflate the compartment. The compartment can be deflated due to outflow of the medium. Medium in- and/or outflow can be accomplished by hand or with a pump, which is preferably computer controlled. Examples of medium are air, contrast liquid or water. In selection of the appropriate medium and/or flexible container, it is preferred that the medium and/or the container can be imaged (i.e. provide contrast with the imaging machine, or "is visible" in the image) with the imaging machine.

According to this embodiment, the method comprises inserting a flexible container in the footwear and subsequently inserting the foot and then scanning. The size of the flexible container is appropriately chosen based on the characteristics of the foot, the footwear and/or the scanning procedures. Before, during or after scanning, the one or more compartments of the flexible container is inflated with the medium. Optionally, one or more are deflated. The flexible container aids in determining the optimal fit of the foot in the footwear.

The invention further relates to an insole designing process using the following steps:
  using the imaging information from the imaging machine;
  determining a space between the foot and an inner surface of the footwear; and
  designing an insole that fills at least part of the space between the foot and the footwear inner surface.

Preferably, the computer uses stored algorithms during the insole designing process, as explained in and can be deduced from the steps below. Preferably, the insole design step uses a visualization module. Such a module enables a human subject, for instance the patient or preferably the health care provider, to evaluate the design process and/or the intermediate or final insole design and possibly apply corrections or adjustments.

The insole design step preferably uses one or more adjustment modules. For instance, the quality of the raw imaging information from the imaging machine may be examined by determining the signal strength and the signal-to-noise ratio. The noise generally consists of a background level (often consistent for a given set-up) plus additional scattering which depends on the type and distribution of the scanned materials. Any signal intensities below the background level, corresponding to very small mass density regions, can generally not be distinguished from the background and can therefore generally not be identified. The signal quality is given by the contrast between the signals of phases of interest, e.g. intensity differences between air and tissue, or air and leather, or tissue and bone or air and bone, where air has zero signal intensity. Phases with little contrast may be difficult to distinguish while large amounts of scattering may diminish the contrast between different phases and consequently negatively affect image signal quality.

The insole designing step may use an image cleaning process. Preferably, a foot-in-footwear scan is corrected for background and—if necessary and possible—for scattering. The Region-Of-Interest (ROI) is preferably automatically determined from the distribution of the signals of the image, specifically from the average decay of the signal in the horizontal plane. Selecting the signal inside the ROI generally reduces the scanned volume to about 30 liters. Using pre-determined phase intensity values, the different phases are preferably distinguished from one another in the scanned volume data and consequently, the different parts of the object (air, foot tissue, foot bone, footwear) can be imaged and identified in 3D.

Determination of the space between foot and footwear is preferably based on the image output of the imaging process. Determining a space between the foot and the inner surface of the footwear preferably involves determining the position of one or more elements of the foot, determining the position of one or more elements of the footwear, and subsequently determining a space between the foot and the inner surface of the footwear. Preferably, the position of the air is also determined. Preferably, determining the position of the foot comprises of determining the position of the hard tissue of the foot and/or determining the position of the soft tissue of the foot. For optimal comfort and fit with the footwear, preferably both are determined. Important examples of hard tissue elements of the foot are bone and nails. In a preferred embodiment, the position of the bones and nails of the foot are determined. Other examples of hard tissue are internal bone structures, external bone structures and metal elements. Important examples of soft tissue elements of the foot are skin, connective tissue, muscles, blood vessels, ligaments and tendons. Fat is a further example. Preferably, at least the position of the skin of the foot is determined. Important examples of elements of the footwear are the inner surface (particularly the inner sole), other footwear surfaces on the inside of the footwear, and the position of the heel. Preferably, at least the position of the inner sole (of the footwear) is determined. As part of the insole designing step, preferably the position of the elements of the foot and/or the footwear is determined, and more preferably their relative positioning.

In a preferred embodiment, the relative position (to each other and/or to air and/or to other foot and/or footwear elements) of the foot bones is determined. This information can be compared with information stored in the computer, for instance information of models of normal relative foot bone positioning.

Preferably, determination of the space is conducted three dimensionally and preferably digitally.

According to the invention, the position of the foot tissue and/or the footwear and/or the air in the image is preferably determined by selecting one or more image layers and/or applying at least some transparency to other image layers. Since different elements of the foot, the footwear and air have a different density, they produce different contrasts. The position of foot tissue and/or footwear and/or air in the image is preferably determined by selecting the contrast range that corresponds to the contrast produced by imaging foot tissue and/or footwear and/or air.

In a preferred embodiment, the air pockets (empty space) within the footwear around the foot are determined. The air pockets are preferably identified from the boundaries of the imaging information of the foot and boundaries of the footwear. This preferably involves determining the boundaries between the contrast of different phases and more preferably determining the foot outer boundary, the footwear outer boundary, the boundaries between foot and footwear, and the empty space (air) within the footwear. Preferably, the boundaries between the foot and the footwear are determined, particularly at positions where the foot meets the footwear (i.e. at positions where no air is present). Preferably, boundaries between the bones and the tissue are additionally determined. Preferably, the insole design process uses the relative position (in 3D) of one or more of these elements. Preferably, the insole design process uses the air pockets inside the footwear, more preferably the air pockets on the inside of the footwear and below the foot, above the inner sole of the footwear and below the foot. Preferably, the insole design process further uses the relative positions of the foot and the footwear, particularly at positions where no air is present. Preferably, the insole design process also uses the relative position (in 3D) of the bones of the foot in comparison with any of the other elements.

Preferably, the lower profile of the insole is constructed by interpolating and fitting a profile through the lower region of the air pockets. Preferably, the positions of the foot and/or footwear are also used for determining the lower profile, for instance for positions where no air pockets are present. At certain positions, there may not be any space or air pockets between the footwear and the bottom of the foot, for instance at positions where they contact each other. At such contact points, there may not be any air or air pocket present. This yields a shape that closely follows the inner sole of the footwear. The upper profile of the insole is preferably constructed by interpolating and fitting a profile through the top (upper) region of the air pockets to yield a shape that follows the contours of the bottom of the foot. Preferably, the positions of the foot and/or footwear are used, for instance for positions where no air pockets are present. Preferably, fitting of the lower profile uses a larger smoothing factor than of the upper profile. We have found this leads to a better fit, likely reflecting that the foot generally has more detail (shape variation, features) than the inside of the footwear. Thus, the upper profile of the insole preferably exhibits more detail than the lower profile, i.e. the lower profile is smoother.

A preferred method uses air pockets in the imaging information for the insole designing process. Specifically, selected air pockets form caveats between the lower part of the foot and upper part of the inside of the footwear. Voxel coordinates of a caveat can be stored as $C_{Caveat}=[x, y, z]_{Caveat}$. We have found it to be helpful to project the caveat coordinates onto the x,y plane in determining the outline of the caveat in 2D. Such projections can be conducted in the z plane, constructing a 3D image of the 2D caveat outlines. The lower profile and upper profile of the caveat are calculated from the lowest and the highest caveat points respectively. This can be mathematically expressed as taking $z_1$=minimum(z) and $z_2$=maximum(z) at each (x,y). This preferred process results in profile coordinates $C_{Profiles}=[x, y, z_1, z_2]_{Profiles}$. The lower profile and upper profile are preferably fitted from these two caveat profiles. Any gaps in the profiles can be interpolated and unwanted features (for instance, due to noise) can be smoothened. This preferably yields a continuous and smoothed, 3D description for the lower and the upper insole profile. The lower profile is preferably more smoothened than the upper profile, as the upper profile preferably retains more details to improve the insole fit. This is preferably accomplished by using different settings for the smoothing parameter. Preferably, the fits are subsequently stored as coordinates $C_{Fits}=[x, y, z_1, z_2]_{Fits}$.

As explained in the embodiment discussed above, a flexible container may be used during the imaging step. In analogy with the use of air pockets, the contrast difference in the imaging information provided by the flexible container can be used in fitting a lower and upper profile through the lower and upper contrast regions of the flexible container to construct a lower and upper profile for the insole.

According to the invention, the anatomic positioning of the foot bones is preferably determined. We have found that serious medical conditions outside the foot-ankle region can be resolved using insoles of the invention, allowing repositioning of the foot skeleton misalignments. Medical conditions often involve body parts that compensate for any asymmetry between both feet, causing a multitude of complaints. For instance, subjects suffering from scoliosis, a sideways curvature of the spine deformity, are almost always fitted therapeutic shoes to correct their overall body skeleton alignment, while subjects suffering from cluster headaches have been successfully treated by custom fitting therapeutic insoles, when the problem was caused by asymmetry between the left and right foot-ankle areas.

Affected areas outside the foot-ankle region often include knees, hips and back, but can extend up the spine to shoulders, neck and head. The feet are the foundation of the skeleton, literally performing the groundwork for the rest of the body. Any misconfigurations will have effects on supported body parts. Foot skeleton problems, such as bone misalignments, leg length discrepancy or general bad posture, all extend upwards along the skeleton, causing misalignments and tension in various muscle groups which try to adjust to the resulting asymmetry. We have found that using insoles of the invention provides for anatomical corrections that may diminish medical complaints. These may be caused by skeletal misalignments, for instance differences in length or positioning of bones. Benefits include relief of chronic pain, better posture and prevention of (further) damage. Additionally, the invention even allows damage due to the bone misalignments to be reversed.

Accordingly, the invention is also directed to determining the anatomic positioning of the foot bones, preferably the relative positioning to each other and/or to other tissue and/or air. This allows for determining if any required anatomical correction of the foot is required. The anatomic positioning of the foot bones can be compared to normal foot bone positioning, for instance retrievable from the computer (like stored in a database in the computer) and/or by a health care provider and any deviation can be identified. Any anatomical correction is preferably determined by comparison to bone positions of healthy subjects. The anatomical correction is preferably translated to an adjustment of the insole design. The translation to insole design adjustments is preferably at least partially based on algorithms stored in the computer. Adjustments to the insole for correction of foot bone positioning are preferably made to specific positions on the upper profile (the top of the insole) and/or in the inner insole structure. The lower profile of the insole is generally fitted with the inside of the footwear. Ultimately, the upper profile of the insole in use ultimately presents the optimal, corrected position of the bottom of the foot. This means that at certain positions some material may be added, providing extra thickness to the insole, for instance to push bones in a different position. It is also possible that material is removed to provide more space to the foot should that be necessary. Further, more or less support may be required at certain position which can be accomplished by providing different structures and/or materials at those positions, on the surface of the upper profile and/or deeper on the inside of the insole and possibly in a wider area. An example is a correction to the insole for flat foot adjustment.

Adjustments to the upper profile and/or the inner insole structure include adding material to or removing material from and/or changing the structure of the insole.

The present invention presents a flexible process for insole design, allowing customization to a high extent.

After determination of the space (between the foot and the footwear, preferably under the foot and above the inner foot bed of the footwear), an insole is designed, preferably digitally. The insole is designed to fill at least part of the space between the foot and the inner surface of the footwear, preferably the inner surface of the footwear underneath the foot (i.e. the inner foot bed of the footwear). Preferably, the insole is designed to cover the inner foot bed of the footwear for at least—preferably part of—the surface (length and width) of the foot.

The insole design process preferably determines for each part of the insole, the thickness and/or the material type to be used. Such determination is based on the size and location of the space, preferably on the bone locations. In a preferred embodiment, the determination uses the functionality of the footwear, from algorithms and/or human expertise. The intended functionality of the footwear may for instance relate to the type of activity the footwear is used for and/or to the correction that is aimed for. Insole production capabilities may further affect the insole design, particularly the choice of material.

The insole comprises one or more materials. One material may for instance be processed in different manners which then results in two (or more) chemically or physically different materials.

In a preferred embodiment, the insole design is based on the fitted profiles. Some details may be restored to the upper profile in a region, for instance if the fit has been smoothened too much, while other details may be further smoothened. Additional adjustments are made to the upper profile for required anatomical corrections to the foot skeleton.

The lower and upper profiles of the insole are preferably based on the above mentioned fitted profiles. In one embodiment of the invention, the fitted upper profile is subsequently combined with the upper caveat values to create a final upper profile for the insole. Such combination with the upper caveat profile after fitting allows for—at least partially—restoring of detailed features that had previously been smoothed out during the fitting process, for instance at the front upper profile of the insole design. In another embodiment, the initial fitting process of the upper profile is less stringent, and, preferably, the upper profile is less fitted compared to the lower profile. Additional adjustments may be made to the upper profile for required anatomical corrections to the foot skeleton, as explained above. This process results in coordinates $C_{Profiles}=[x, y, z_1, z_2]_{Profiles}$. Additional smoothing may be required to create a uniform design without unwanted roughness, such as spikes. This is preferably done by convolution of $C_{profiles}$ with a 2D-Gaussian filter.

Preferably, the distance between lower and upper profiles is (preferably subsequently) checked for minimum and/or for maximum insole thickness requirements. Adjustments of the distance are preferably made by moving the profiles further apart or closer. Preferably both profiles at any point are separated with at least a minimum distance. If the distance between any points on the lower versus the upper profile of the image becomes too small (the profiles are too close or even intersect), then preferably at least part of one or more of the profiles are moved over a distance such that a minimal distance between the profiles is reached. In one embodiment, the thickness of the entire insole is increased, in another part of the thickness of the insole is increased. Consequently, the insole design preferably has at least a minimal thickness. Likewise, the distance between the profiles is checked not to exceed the maximum insole thickness. Preferably, the minimal insole thickness is at least 0.1 mm, more preferably at least 0.5 mm, most preferably at least 1 mm. Preferably, the maximum insole thickness is at most 100 mm, more preferably at most 60 mm, most preferably at most 10 mm, and particularly preferred is at most 5 mm.

Preferably, the edges of the insole design are trimmed, more preferably with at least 0.1 mm at least at some positions (for instance preferably at least 5%, and for instance preferably at most 90% of the perimeter) along the edge of the insole, and more preferably at most 10 mm along the rim. In one embodiment the insole size is reduced with a percentage, for instance from 0.5 to 5%. Reducing the outside of the insole profiles will allow for easier placement of the final insole inside the footwear. Edges may also be trimmed to give them a particular shape. For instance, the edge may be made less sharp, rounder or curved, allowing for easier placement in the footwear.

To provide for an inner insole structure, the lower and upper profiles are preferably connected. To connect both profiles, preferably, a band of additional points is created between the outlines of the lower and upper profiles of the insole design. These additional points form a connecting band. The points of the band are preferably spaced with the same resolution as those of the profiles. The set of lower and upper profiles and the connecting band together form a closed 3D inner insole volume with coordinates $C_{Design}=[x, y, z]_{Design}$. Preferably, vertices $V_{Design}=[x, y, z]_{Design}$ and faces $F_{Design}=[\#1,\#2]_{Design}$ are constructed from the points of the inner sole volume. The vertices list the unique, ordered coordinates of the points and the faces list the connections between points, which preferably are calculated by triangulation. Following these steps, the closed inner insole volume now consists of a set of adjoining triangles. Preferably, a 3D boundary profile is subsequently calculated that spans the vertices with a certain tightness. The tightness parameter value ranges from 0 for the convex hull (largest surrounding volume) to 1 for the most compact object (smallest volume containing all vertices). A tightness parameter value is used as close to 1 as possible such that preferably no leakage (gaps in the surrounding profile) occurs. Values closer to 0 provide more smoothening to the profile, as details are engulfed within the resulting object. The resulting 3D object has known surface area and known volume. Preferably, the insole design is finalized by converting the voxel units of the vertices to millimeters, distances such as local insole thicknesses to mm, surface area to $mm^2$, and volume to $mm^3$. A selection may be made from a list of available inner insole structures, based on requirements that are programmed and/or pre-set by an operator. The subject, the health care professional and/or the computer may select these requirements from factors such as the type of printing material, type of footwear, functionality, body weight, openness for moisture and air migration (breathing). The result of the insole design is preferably validated by performing authentication checks. Subsequently, the design data (vertices and faces) are preferably written to an STL file.

The process can be repeated using the imaging data for the other foot-in-footwear, as appropriate.

The invention further relates to an insole preparation process using the following steps:
  providing the insole design to a printer machine; and
  printing the insole with the printer machine.

Preferably, the printer machine is fed with the design of the insole to be printed, which is preferably based on the initial imaging process. The insole design includes details on the dimensions of the insole (including outer shape, length and, width and importantly the thickness) and on the materials to be used (i.e. at what location to use which materials) and preferably an indication of its hardness, flexibility and elasticity.

The information on the outer and inner insole design is preferably stored as an STL file which contains vertices (coordinates) and faces (connections). The printer machine of the invention may use a cutting method but preferably uses an additive process by adding successive layers of material to create a three dimensional object, in the case of the present invention of an insole. These printer machines are often called 3D printers.

Preferably, the printer machine for production of the insole is a three dimensional (3D) printer. Production in a three dimensional printer is often called 3D printing.

The arrangement of the printed materials is determined by the outer shape of the insoles and the inner insole structure. The arrangement may use a single material in the same pattern throughout the whole insole or use one or more materials arranged in different denseness and/or patterns. It is often preferred to start with the simplest case closest to fulfilling the requirements of the insole and then addressing any remaining discrepancies by adjusting material properties and adding complexity such as printing with additional patterns, varying the material denseness and/or additionally using other materials. Selection of printing materials may also be limited on what the available printing techniques support. The final design lies in a spectrum of complexity options between the two extremes of homogeneous to heterogeneous.

Available inner insole structures include (but are not limited to) continuous and perforated types, or in other terms: areas surrounding optional holes. Within these areas a pattern can be printed with varying degrees of denseness to influence the material properties. A pattern consists of layered polygons, which for simple cases are triangles, squares, pentagons, hexagons etc. While layers can be stacked one above the other, for most designs they have different orientations. For instance, layers may be shifted or rotated with respect to another. Honeycomb structures, which are regularly shifted layers of hexagons, are beneficial for these purposes.

Conventional desktop 3D printers use melted plastic to build a model, but there are many other materials that can be 3D printed, which require their own type of 3D printer. The custom insole can be printed using a range of materials, which include (but are not limited to) synthetic plastics, solid foams, textiles, paper and metal. The preferred types of material are photopolymers and flexible resins. Plastics commonly used in 3D printing are synthetic polymers of various compositions with both viscous and elastic properties, often copolymers or a mix of polymers. These include thermoplastic elastomers (TPE), synthetic rubbers, glues, synthetic textiles, foams and composites of these materials, such as carbon-fiber reinforced polymers. Natural non-synthetic materials can also be used for the 3D printing of insoles, such as cellulose fibers and metal powders. Thermoplastic elastomers, such as ethylene-vinyl-acetate (EVA), are amorphous polymers with viscoelasticity, being both thermoplastic and elastomeric. Synthetic rubbers, such as polychloroprene (Neoprene), are elastomers with rubber-like properties, simulating natural rubbers such as polyisoprene. Synthetic glues can be monomer glues, such as cyanoacrylate (superglue), or made from a wide range of polymers. Synthetic textiles, such as low friction fabrics and Gore-Tex—stretched polytetrafluoroethylene (PTFE, i.e. Teflon) foil—can be smoother, stronger and more water-proof than natural products and are widely used for such things as medical textile, sportswear, motorcycle suits and sail clothing. Foams, such as expanded polystyrene (styrofoam) can be printed with varying permeability, ranging from open, highly porous and light weight to closed with small air bubbles in a solid, dense matrix—or as a hybrid, combining stiff metal with soft, porous rubber. Paper models are printed in 3D by gluing sheets of paper into layers, which are precisely and finely cut and colored with ink, whereas metal models are printed through laser sintering aluminum, brass, bronze, steel, silver, gold and platinum powder.

The types of printers used for the custom made insole vary in printing technology, which in turn depends on the materials used. These include (but are not limited to) the ones listed in Table 1. The preferred methods are Fused Deposition Modeling (FDM), which can handle a wide range of materials, and Digital Light Processing (DLP), which is newer and more maintenance-cost-effective than the common Stereolithography (SLA).

TABLE 1

| 3D printer type | Available technologies | Suitable materials |
|---|---|---|
| Extrusion | Fused Deposition Modeling (FDM) | Thermoplastics, eutectic metals, edible materials, rubbers, plasticine, metal clay (including precious metal clay) |
| | Fused Filament Fabrication (FFF) | |
| | Robocasting or Direct Ink Writing (DIW) | Ceramic materials, metal alloys, cermet, metal or ceramic matrix composite |
| Light polymerized | Stereolithography (SLA) | Photopolymer |
| | Digital Light Processing (DLP) | Photopolymer |
| Powder Bed | Powder bed & inkjet head 3D printing (3DP) | Almost any metal alloy, powdered polymers, plaster |
| | Electron-Beam Melting (EBM) | Almost any metal alloy including titanium alloys |
| | Selective Laser Melting (SLM) | Titanium alloys, cobalt-chrome alloys, stainless steel, aluminum |
| | Selective Heat Sintering (SHS) | Thermoplastic powder |
| | Selective Laser Sintering (SLS) | Thermoplastics, metal powders, ceramic powders |
| | Direct Metal Laser Sintering (DMLS) | Almost any metal alloy |
| Laminated | Laminated Object Manufacturing (LOM) | Paper, metal foil, plastic film |
| Powder Fed | Directed Energy Deposition (DED) | Almost any metal alloy |
| Wire | Electron Beam FreeForm Fabrication (EBF[3]) | Almost any metal alloy |

Multiple 3D printing techniques are available, including sintering and Digital Light Processing (DLP). Sintering uses lasers to heat up polymer material. DLP uses light and photopolymers. DLP is relatively cheap and can be flexibly moved and placed in view of its generally smaller size.

Preferred materials for production of the insole have a hardness of at least 20. Preferably, the hardness is less than 120, more preferably less than 100, most preferably less than 90. According to the invention, shore hardness is determined using the ASTM D2240 type A scale. Sometimes these values are represented as 20A, 120A, 100A and 90A. An example of a suitable material for preparing the insole of the invention by sintering is TPU 92 wherein TPU represents thermoplastic Polyurethane and 92 represents Shore hardness of 92A and is available as "rubberlike" from iMaterialise, Leuven, Belgium. Another suitable material that is processed using DLP is Formlabs Flexible of the company Formlabs, Sommerville, Mass., USA which has an elongation of 90%, tensile strength of 5.9-6.6 mPa and hardness of 80-90A.

After the insole has been produced, the insole is preferably inserted in the footwear. Subsequently, the foot is inserted in the footwear. This allows for instance for verification that indeed the fit between foot and footwear is optimal. Optionally, a further image scan can be made of the foot in the footwear with the insole.

The present invention preferably uses a computer, preferably connected to a display. The computer is preferably adapted to determining a space between a foot and an inner surface of the footwear using imaging data and preferably the computer is adapted to designing an insole that fills at least part of the space between the foot and the footwear inner surface.

According to the invention, the computer preferably uses software that is preferably loaded on machine readable medium, such as memory card or disk. Preferably, the computer implemented method comprises one or more of the following modules with the indicated functionality:

scanning module: to direct the X-ray machine to scan the object and collect the scan result (image of object). This module is preferably integrated in the imaging machine;

input module: to receive and/or combine the input (image of object, optionally with flexible container) and optionally convert the information to another format to makes the input suitable for further processing in the analysis module;

algorithm module: to store and provide algorithms for calculation of the optimal insole design;

analysis module: to convert the image input using the algorithms to the optimal insole design;

adjustment module (optional, but preferred): to adjust the insole design, manually by the subject or preferably the health care provider and/or automatically by a computer;

visualization module (optional, but preferred): to display the scanned object and/or the (optimal) insole design;

reporting module: to report status information on scan, calculation and/or print processes during the process or from stored form after the process, and to report and make available the (optimal) insole design; and/or output module: to make the insole design available digitally.

In support of these modules, the computer implemented method uses other modules as follows:

file management module: to save, retrieve and/or delete information; and software management module: to test the software, to provide user-interface, and/or to ensure IP safety.

We have found the present invention is particularly useful for improving the fit between foot and footwear and has general applicability.

The invention allows for preparation of insoles for regular footwear but also for special footwear that can compromise a foot. Such special footwear requires adjustment of the foot or body and examples are a high heeled shoe, a pointed footwear nose, orthopedic shoes, a narrow shoe last, high performance sports shoes, running shoes, skates, surf boards, boots, sports boots, ski boots and/or otherwise flat-soled slippers.

Similarly, the invention allows for preparation of insoles for regular feet or for special feet to improve the fit with the footwear. Such special feet include medically compromised feet, such as for instance with bone and/or soft tissue diseases or malformations.

The invention further relates to a system comprising an imaging machine, a computer and a printer machine. The imaging machine, the computer and the printer machine are preferably connected in an electronic network. Preferably, the imaging machine is adapted for producing images of a foot and a footwear. Preferably, the computer is adapted for determining a space between the foot and the footwear from the images. Preferably, the printer is a three dimensional printer adapted for producing an insole for the space between the foot and the footwear. The system preferably comprises at least one piece of footwear. If the system comprises the more preferred two pieces of footwear, then the weight-bearing of the footwear can be better taken into account while the overall imaging efficiency is increased. Preferably, the footwear is present in the machine as a foot-in-footwear and, more preferably, the system comprises two sets of foot-in footwear. Preferably, the imaging machine produces three dimensional images. Preferably, the imaging machine is an X-ray machine. Preferably, the 3D printer is adapted insole is three dimensional.

DETAILED DESCRIPTION OF THE FIGURES

Figure 1:
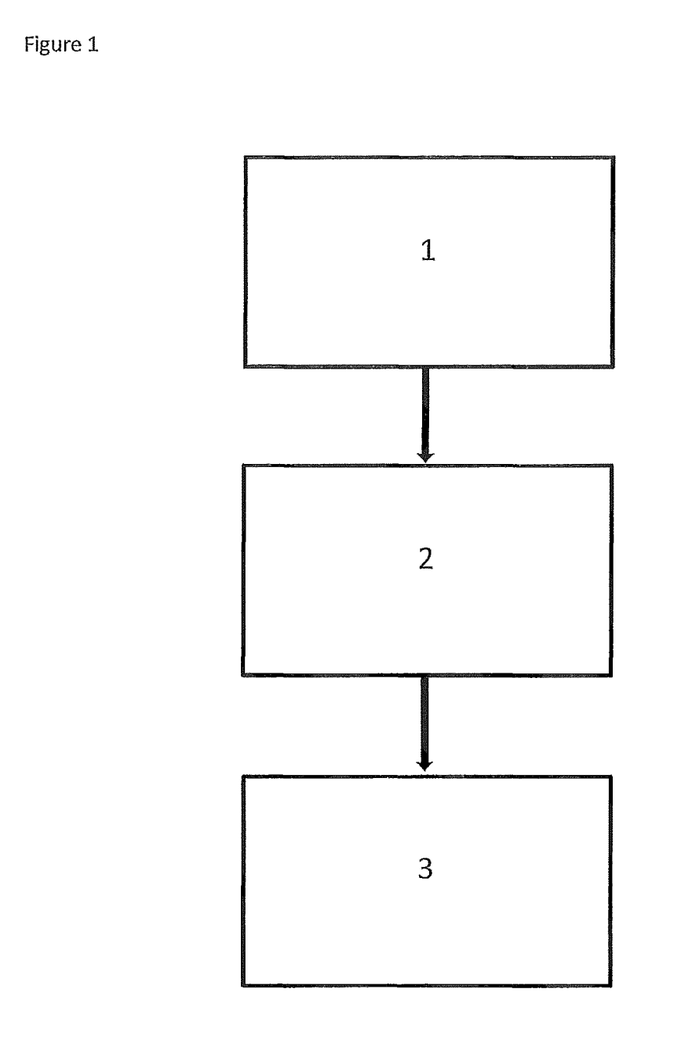
FIG. 1 shows a graphical representation of the steps of the method of the present invention.

FIG. 1 shows a flow diagram of a preferred embodiment of the invention. In step 1, the foot is inserted in footwear and scanned in the CurveBeam pedCAT® imaging machine. In step 2, the image is provided for design of an insole. In step 3, the insole design is provided for preparation of the insole.

Figure 2:
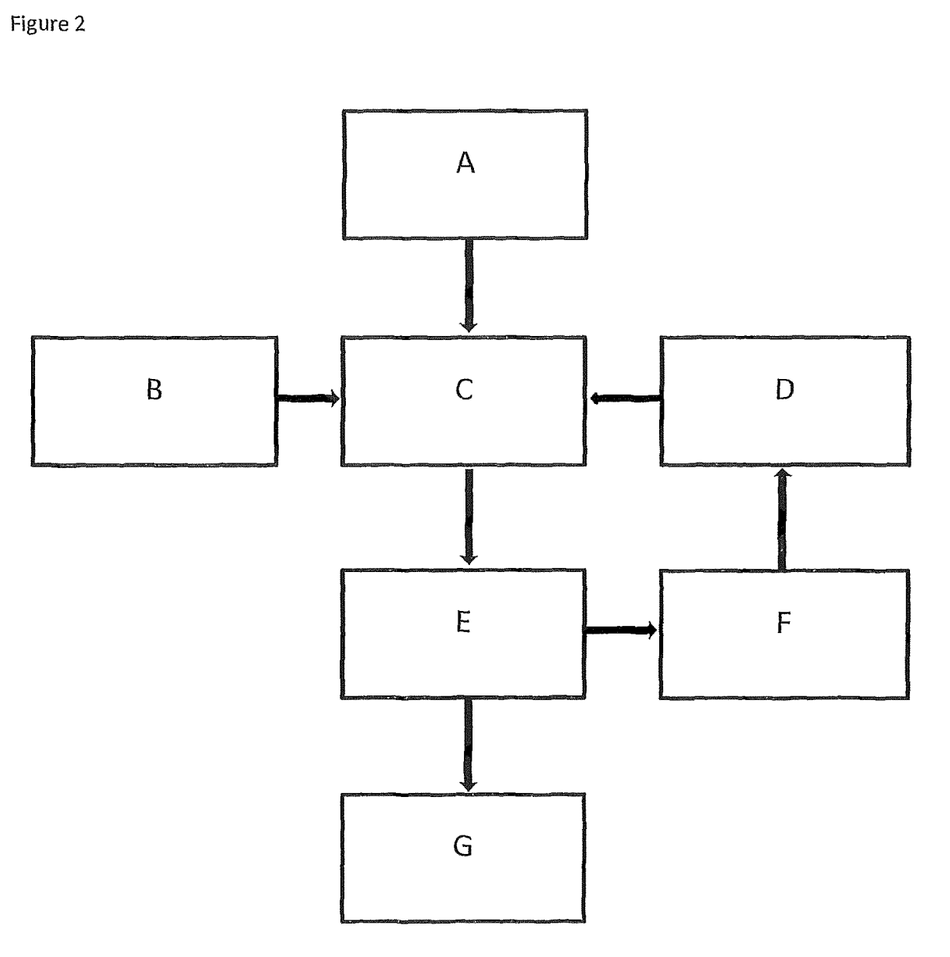
FIG. 2 shows a graphical representation of the computer modules used in the present invention.

FIG. 2 shows a flow diagram of a preferred embodiment of step 2 of the invention.

A. represents the input module to receive the image of the object, optionally with flexible container for further processing in the analysis module;

B. represents the algorithm module to provide algorithms for calculation of the optimal insole design;

C. represents the analysis module to convert the image input using the algorithms into the optimal insole design;

D. represents the adjustment module allowing an expert to manually adjust the insole design;

E. represents the reporting module to provide the insole design;

F. represents the visualization module to display the scanned object and/or the insole design; and G. represents the output module to make the insole design available digitally, for instance for printing in a three dimensional printer.

Figure 3:
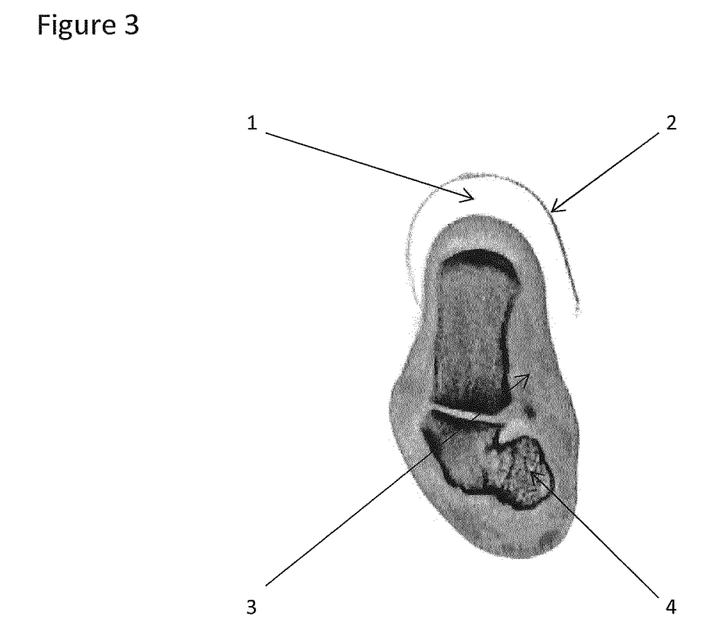
FIG. 3 shows a graphical representation of an image of the ankle.

FIG. 3 shows a 2D image of a horizontal slice at ankle height with air (1), footwear (2), tissue (3), and bone (4) discernible.

Figure 4:
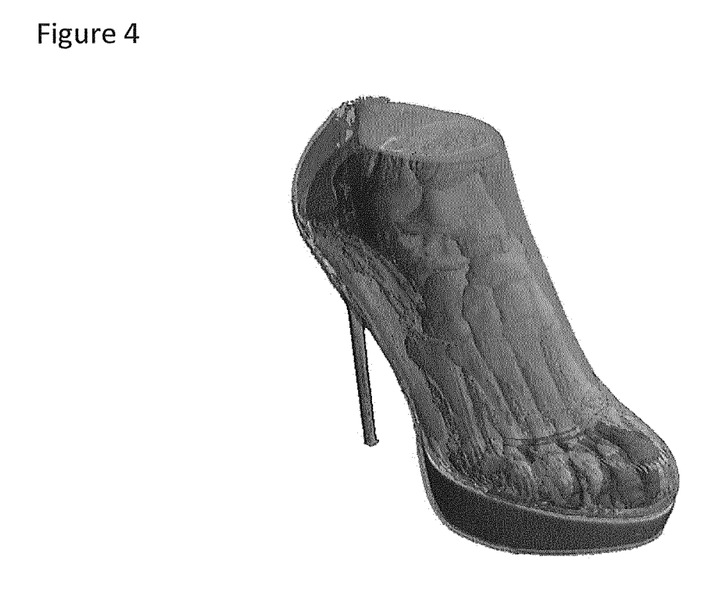
FIG. 4 shows a graphical representation of a foot in a high heeled shoe.

FIG. 4 shows 3D image of a foot inside footwear; using different image transparencies, the toes and toe nails can be distinguished at the bottom right of the figure, while the foot bones can be distinguished higher up. This figure illustrates that the image generated according to the invention described above, allows for identifying different parts of the foot (like skin, bone, soft tissue, fat), the footwear and/or the air of the foot in footwear object from the different densities of the material. These different densities are reflected in different contrast in the image. By applying transparency to one or more layers and/or selecting particular contrast ranges, different tissues can be identified and their position determined.

Figure 5A:
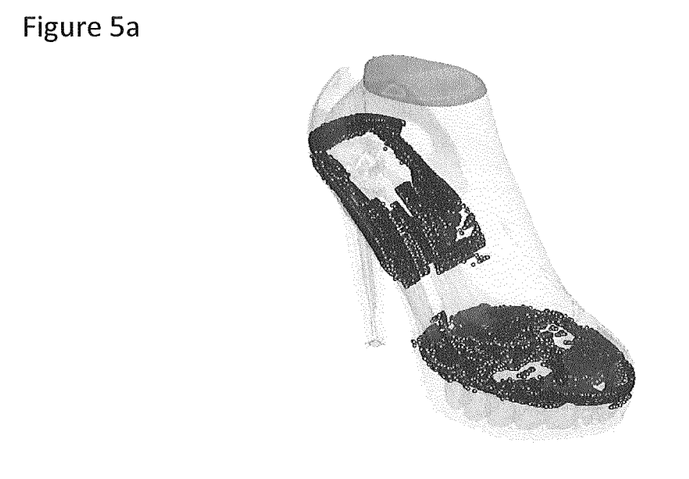
FIG. 5a shows a graphical representation of an image with darkened air pockets inside footwear underneath a foot.
Figure 5B:
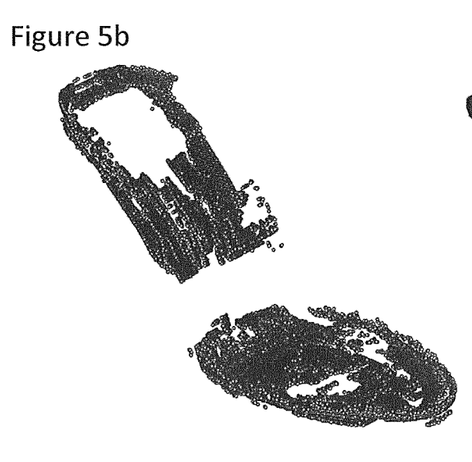
FIG. 5b shows a graphical representation of the lower profile of air pockets inside the footwear underneath a foot.
Figure 5C:
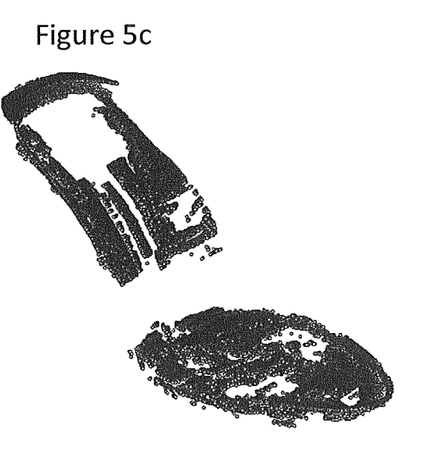
FIG. 5c shows a graphical representation of the upper profile of air pockets inside the footwear underneath a foot.
Figure 5D:
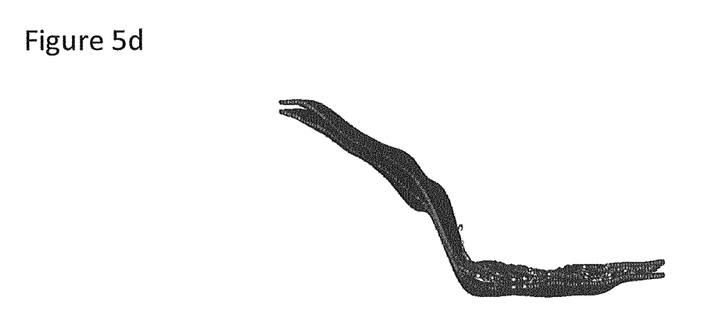
FIG. 5d shows a graphical representation of the combined lower and upper profile of air pockets inside the footwear underneath a foot.

FIG. 5*a* shows the air pockets inside the footwear as identified from the scan. It is noted that the white areas represent positions where no air was detected and for instance the bottom of the foot directly contacted the inner sole of the footwear. FIG. 5*b* shows the lower profile of the air pockets inside the footwear underneath the foot (which itself is not shown) while FIG. 5*c* shows the upper profile of the air pockets in the footwear underneath the foot (which itself is not shown). FIG. 5*d* shows the combined lower and upper profile of the air pockets between the footwear (which itself is not shown) and the foot (which itself is not shown), the distance between the lower and upper profile representing the space between the foot and an inner surface of the footwear.

Figure 6A:
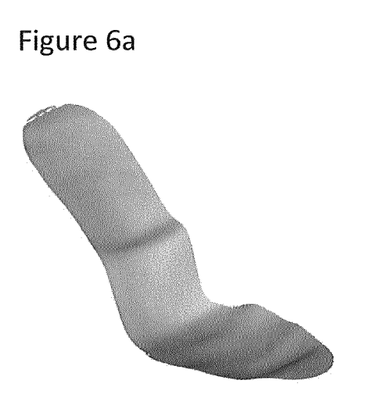
FIG. 6a shows a graphical representation of the lower profile of the insole.
Figure 6B:
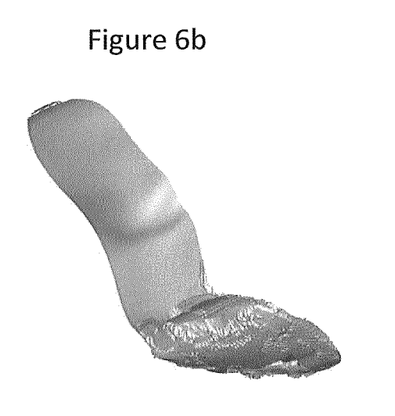
FIG. 6b shows a graphical representation of the upper profile of the insole.
Figure 6C:
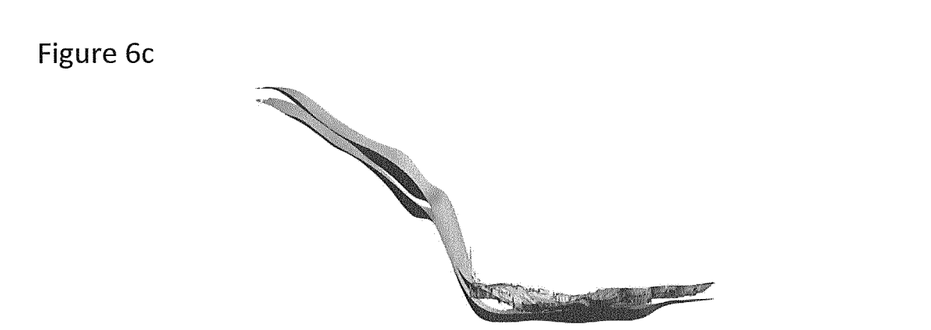
FIG. 6c shows a graphical representation of both the lower and the upper profiles of the insole.

FIG. 6*a* show the lower profile of the insole that is designed from the lower profile as shown in FIG. 5*b*, while FIG. 6*b* shows the upper profile for the insole that is designed from the upper profile as shown in FIG. 5*c*. FIG. 6*c* shows the combination of the lower and upper profiles for the insole profiles with a space between the two profiles representing the space between the foot and an inner surface of the footwear of the subject.

Figure 7:
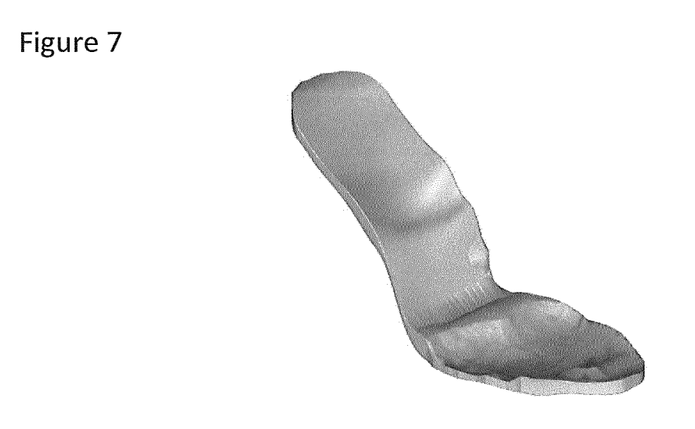

FIG. 7 shows the insole design with lower and upper profile and a rim. This design has a minimal thickness and an inner structure. The data file of this design can be sent to a 3D printer for printing.

Example

The feet of a woman suffering from discomfort and pain when wearing high heel shoes, particularly over a longer period of time, were imaged in a CAT-scan whilst wearing the shoes. The subject stood still in the CurveBeam pedCAT® machine in the high heels with normal posture, with both feet positioned parallel and with the feet bearing full weight during the scan which took about two minutes. The scan was performed bilaterally with a low dose X-ray beam. The imaging data was processed and stored as a set of compressed DiCOM files.

A computer loaded with software uses the DiCOM data and designed insoles for both feet. First, the computer constructed a 3D image of the scanned feet in shoes. Then, the profiles of the inner shoe, outer foot and foot skeleton were extracted, for each foot-in-shoe separately. The subsequent insole design process yielded a profile of the shoe bed, a profile of the bottom of the foot, and the extent of foot bone misalignments. A precise fit between the inside of the shoe and the foot bottom was computed, as well as the required positional correction to the foot bones. The software then designed insoles that followed the exact contours of both the shoes and the feet (to provide comfort and support through a perfect fit) and provide anatomical support (through adjustments to the upper profile of the insole). The software on the computer determined the anatomical corrections by comparing the measured bone positions to existing foot skeleton positional models for healthy feet. The anatomical corrections to the foot bone positions were translated into adjustments to the insole support, such as local patches of extra thickness.

The scan procedure can be augmented with a flexible container that is inserted between the foot sole and the shoe and—at least partially—inflated with air or a liquid before scanning. The flexible container can be used to enhance the scan and image quality and improve the fit. Inflation of the flexible container is manually conducted but is preferably automated.

The computer produced insole designs were judged visually by the podiatrist, before subsequently being sent to a 3D printer. The printing generally depends on the design structure, printing materials and printing technique). The resulting insoles were a perfect custom fit for the scanned feet with shoes combination, with additional features to correct for misalignments of foot bones.

The female subject received two insoles, a left and a right one. The insoles each fitted in their respective shoe. The invention provided a multitude of benefits, greatly reducing various discomforts, drastically increased comfort of wearing her high heels whilst standing, walking, and climbing stairs, and allowing the subject to wear the shoes longer. The anatomical support reduced pain caused by foot bone misalignment. The custom fit insoles functioned well as interface between foot sole and inner shoe so that the shoe became an extension of the foot. Additionally, the subject's posture was independently judged to have been improved.

The invention claimed is:

1. A method of preparing an insole for a foot inserted in footwear by:
   inserting the foot in the footwear;
   positioning the foot, inserted in the footwear, in an imaging machine;
   scanning the foot inserted in the footwear with the imaging machine;
   determining a space between the foot and an inner sole of the footwear; and
   designing an insole that fills at least part of the space between the foot and the inner sole of the footwear.

2. The method according to claim 1, wherein the insole design is provided to a printer machine to produce the insole.

3. The method according to claim 1, wherein the footwear is in a fixated position in the imaging machine during the scanning.

4. The method according to claim 1, wherein the imaging machine produces a digital, three dimensional image of the foot in the footwear.

5. The method according to claim 1, wherein first a flexible container is inserted in the footwear and subsequently the foot is inserted in the footwear.

6. The method according to claim 1, wherein the flexible container has one or more compartments that are inflated with a medium before, during or after the scanning with the imaging machine.

7. The method according to claim 1, wherein determining the space between the foot and an inner sole of the footwear comprises of determining the position of one or more bones and/or soft tissue and/or skin of the foot and the inner sole of the footwear.

8. The method according to claim 1, wherein determination of the space is conducted three dimensionally and digitally.

9. The method according to claim 1, wherein the image of the foot in the footwear is presented on a display.

10. The method according to claim 1, wherein a second foot inserted in a second footwear is positioned in and scanned with the imaging machine, wherein a space between the second foot and an inner sole of the second footwear is determined, and an insole that fills at least part of the space between the second foot and the second footwear inner sole is designed.

11. The method according to claim 1, wherein the left foot in footwear and the right foot in footwear are scanned with the imaging machine at the same time.

12. The method according to claim 1, wherein determining a space between the foot and the inner sole of the footwear comprises:
   using image data from the imaging machine; and
   generating three dimensional profiles of the footwear in the foot.

13. The method according to claim 1, wherein designing the insole that fills at least part of the space between the foot and the inner sole of the footwear comprises generating a digital three dimensional image of the insole that has a lower profile that follows the inner sole of the footwear, that has an upper profile that follows the bottom of the foot, and that has an inner insole structure that connects both profiles.

14. The method of claim 1, wherein the imaging machine produces an X-ray computed tomography scan.

15. A System comprising an imaging machine, a computer and a printer machine which are connected in an electronic network, wherein the imaging machine is adapted for producing a three dimensional image of a foot in a footwear, the computer is adapted for determining from the image a three dimensional space between the foot and an inner sole of the footwear, and the printer is a three dimensional printer adapted for producing an insole for the space between the foot and the inner sole of the footwear.

16. The system according to claim 15, wherein the imaging machine comprises at least one piece of footwear.

17. The system according to claim 15, wherein the imaging machine is an X-ray computed tomography scanner.

* * * * *